Figure 1:
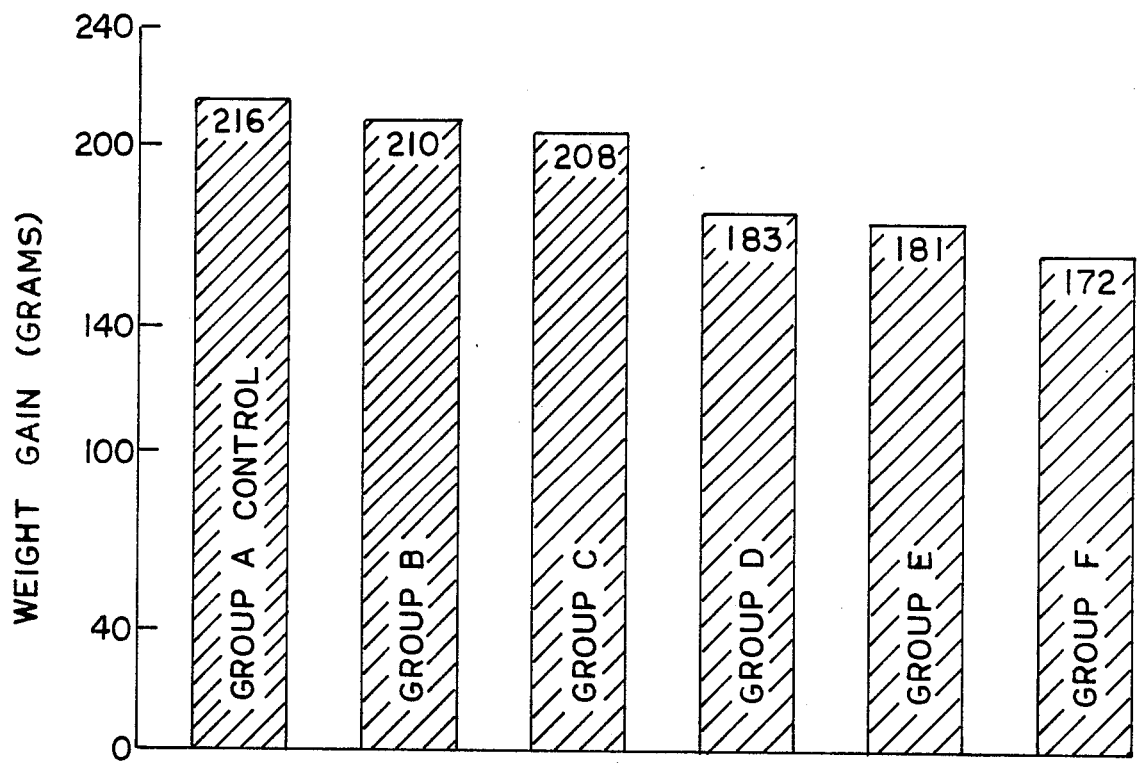

United States Patent [19]

Stanko

[11] Patent Number: 4,812,479

[45] Date of Patent: Mar. 14, 1989

[54] METHOD FOR PREVENTING BODY FAT DEPOSITION IN MAMMALS

[75] Inventor: Ronald T. Stanko, Pittsburgh, Pa.

[73] Assignee: The Montefiore Hospital Society of Western Pennsylvania, Inc., Pittsburgh, Pa.

[21] Appl. No.: 901,402

[22] Filed: Aug. 28, 1986

Related U.S. Application Data

[63] Continuation-in-part of Ser. No. 736,234, May 21, 1985, Pat. No. 4,645,764, which is a continuation-in-part of Ser. No. 529,403, Sep. 6, 1983, Pat. No. 4,548,937, which is a continuation-in-part of Ser. No. 346,181, Feb. 9, 1982, Pat. No. 4,415,576, which is a continuation-in-part of Ser. No. 249,812, Apr. 1, 1981, Pat. No. 4,351,835.

[51] Int. Cl.$^4$ .................... A61K 31/11; A61K 31/19
[52] U.S. Cl. ................................. 514/557; 514/693
[58] Field of Search .................... 514/251, 693, 557

[56] References Cited

U.S. PATENT DOCUMENTS

| | | | |
|---|---|---|---|
| 4,158,057 | 6/1979 | Stanko | 424/252 |
| 4,351,835 | 9/1982 | Stanko | 424/252 |
| 4,548,937 | 10/1985 | Stanko | 514/251 |
| 4,645,764 | 2/1987 | Stanko | 514/251 |

OTHER PUBLICATIONS

Chemical Abstracts 67:19055b (Gershbein), 1967.
Chemical Abstracts 71:121284v (Williamson et al.), 1969.

*Primary Examiner*—Leonard Schenkman
*Attorney, Agent, or Firm*—Harry B. Keck

[57] ABSTRACT

A method for reducing the weight gain in an animal by orally administering over a prolonged period a therapeutically effective amount of dihydroxyacetone to which may be added riboflavin. The method also includes administering dihydroxyacetone and/or pyruvate in therapeutically effective amounts to increase the glycogen store in the liver.

8 Claims, 1 Drawing Sheet

METHOD FOR PREVENTING BODY FAT DEPOSITION IN MAMMALS

CROSS-REFERENCES TO RELATED APPLICATION

This application is a continuation-in-part of application Ser. No. 736,234, filed May 21, 1985 now U.S. Pat. No. 4,645,764 which is a continuation-in-part of application Ser. No. 529,403, filed Sept. 6, 1983, now U.S. Pat. No. 4,548,937 which is a continuation-in-part of application Ser. No. 346,181, filed Feb. 9, 1982, now U.S. Pat. No. 4,415,576 which is a continuation-in-part of application Ser. No. 249,812 filed Apr. 1, 1981, now U.S. Pat. No. 4,351,835.

BACKGROUND OF THE INVENTION

In U.S. Pat. No. 4,158,057 a method is described for preventing the accumulation of excessive fatty deposits in the livers of mammals. It has long been known that ingestion of ethyl alcohol in mammals, including man, frequently results in the accumulation of excessive fatty deposits in the liver. In many cases, this accumulation tends to become irreversible and may lead to serious consequences, particularly alcohol-induced hepatitis and, ultimately, cirrhosis.

The invention described in the aforesaid U.S. Pat. No. 4,518,057 resides in the discovery that excessive fatty deposits in the liver can be reduced or prevented from occurring by administering a therapeutic composition consisting of a mixture of pyruvate and dihydroxyacetone to which may be added riboflavin. These substances are natural metabolites which occur in the body as a result of normal digestive processes. Heretofore, however, there has been no appreciation of any correlation between the accumulation of fatty deposits in the liver, usually due to the ingestion of alcohol, and the accumulation of fat in other parts of the body.

SUMMARY OF THE INVENTION

It has been found, quite surprisingly, that dihydroxyacetone disclosed in U.S. Pat. No. 4,158,057, when administered for a relatively long period of time, at least 15 days or more, results in a reduction of the rate of hepatic triglyceride generation and body fat deposition for a given diet. Dihydroxyacetone is thus useful for impeding overweight conditions in mammals, with or without ingestion of ethanol.

Additionally, it has been found that prolonged ingestion of dihydroxyacetone with or without riboflavin, increases the glycogen-storage capabilities of the liver. Stored glycogen is thus increased for subsequent release into the bloodstream. Stored glycogen has been reported to increase the performance and endurance of athletes.

A further surprising discovery of the present invention is that there is a decrease in the total body fat with a secondary inhibition of weight gain in mammals. Prolonged ingestion of dihydroxyacetone alone or a mixture of dihydroxyacetone and pyruvate, with or without riboflavin, actually changes the body composition to the extent that body fat is actually decreased by the inhibitory effect of the lipotropic agent on fat metabolism.

Figure 2:
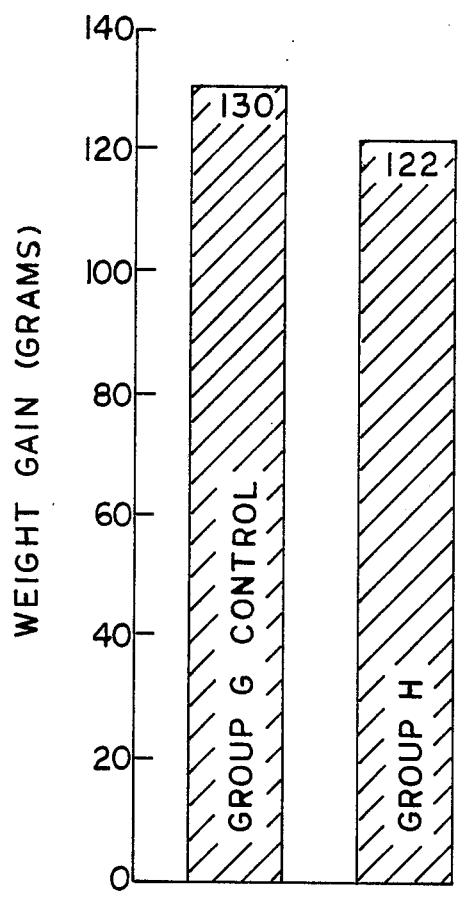
Figure 3:
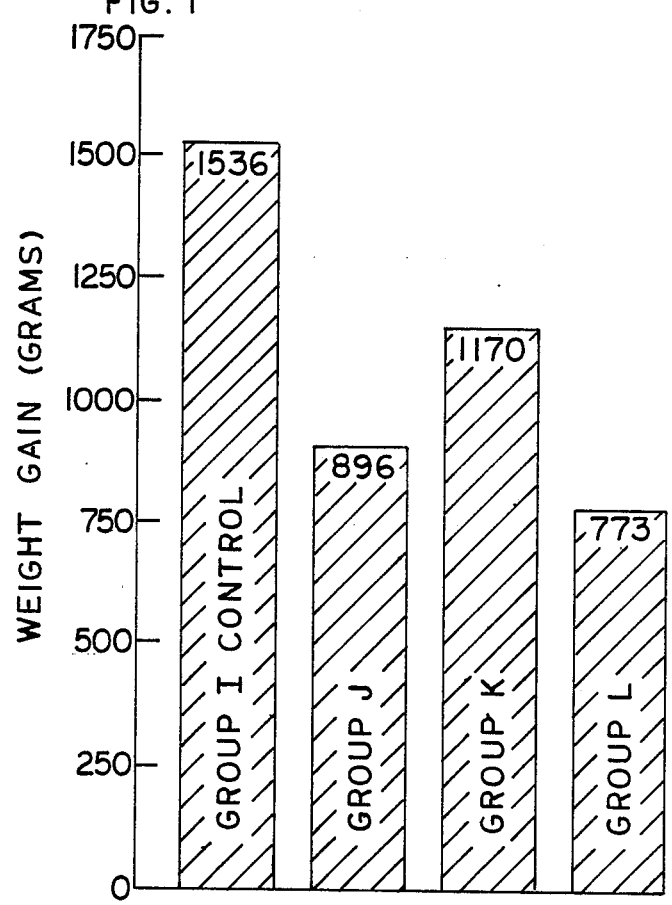

The above and other objects and features of the invention will become apparent from the following detailed description taken in connection with the accompanying drawing which forms a part of this specification, and in which:

FIGS. 1, 2 and 3 are bar graphs illustrating the effect of the present invention on weight gain.

Heretofore, as described in my early U.S. Pat. No. 4,158,057, pyruvate and dihydroxyacetone were found equally ineffective when used alone, but when used in combination, the mixture of these two agents produces a marked reduction in the fatty acid concentration in mammalian livers. The addition of riboflavin to the mixture further enhances the effect. Pyruvate (pyruvic acid-$CH_3COCOOH$) is a product of the metabolism of glucose and some amino acids, while dihydroxyacetone (($CH_2OH)_2CO$) is a product of the metabolism of fatty acids and certain amino acids. These substances are, therefore, both natural metabolites which are normally present in the body, while riboflavin (Vitamin B2) is also present in the body. All of the substances, therefore, are natural products which are normally harmless.

To demonstrate the efficacy of the present invention, a group of experiments extended over a period of 28 days, the results of which are shown in FIG. 1. Rats were divided into six groups ranging from 6 to 9 in number. A standard laboratory diet containing 15% protein, 28% fat and 57% carbohydrate was fed to the rats. The first group (Group A) was fed the standard laboratory diet to which 248 grams of dextrin per 1000 grams of diet was added. Group A was designated a control group. The second group (Group B) received the same diet as Group A but with the addition of 12.4 grams of riboflavin per 1000 grams of diet. The third group (Group C) received the standard laboratory diet to which was added 124 grams of dextrin per 1000 cubic centimeters of the diet and 124 grams of dihydroxyacetone per 1000 grams of diet. The fourth group (Group D) received the standard laboratory diet to which was added 124 grams of pyruvate per 1000 grams of diet and 124 grams of dextrin per 1000 grams of diet. The fifth group (Group E) received the standard laboratory diet to which was added 124 grams of pyruvate per 1000 grams of diet and 124 grams of dihydroxyacetone per 1000 grams of diet. The sixth group (Group F) received the same diet as Group E but with the addition of 12.4 grams of riboflavin per 1000 grams of diet.

As shown in FIG. 1, Group A, control, experienced a weight gain of 216 grams in 28 days which, when compared with the weight gain of 210 grams by the animals in Group B, shows an insignificant difference in the weight gain. The effect of dihydroxyacetone alone in the diet can be seen from the animals comprising Group C which experienced a weight gain of 208 grams. This shows an inhibition of weight gain of 8 grams as compared with control. With respect to the animals comprising Group D, the result was a weight gain of 183 grams as compared with control at 216 grams shows a another inhibition against weight gain. Surprising and similar results were discovered by comparing the weight gain of 181 grams by Group E with the weight gain of control which demonstrates that pyruvate alone is therapeutically effective for weight inhibition substantially to the same extent that the therapeutic mixture of pyruvate and dihydroxyacetone is effective as shown by comparing the weight gains by control Group A and Group E. The inhibition against weight gain is also shown by comparing the results of Group F at 172 grams versus control, Group A, at 216 grams. This shows that the addition of riboflavin in a mixture of pyruvate and dihydroxyacetone in the diet increases the effect against an expected weight gain. The addition of only riboflavin to the diet as shown by comparing Group B with control, reveals a 6-gram difference; whereas the addition of riboflavin to the mixture of pyruvate and dihydroxyacetone in the diet as shown by the results of Group F as compared with Group E shows a 9-gram loss for an expected weight gain.

Similar results are demonstrated by the bar graph of FIG. 2 in which Group G was the control group. Group H received the same diet as control, Group G, but with the addition of 124 grams of dihydroxyacetone per 1000 grams of diet and 124 grams of dextrin per 1000 grams of diet. The experiment extended over a period of 28 days. Groups G and H each comprised 13 rats. The animals were fed the same standard laboratory diet except as just described. The inhibition against a weight gain was small as seen by a comparison of the bar graphs for Group G with Group H. However, with each of the Groups G and H there was a standard error of less than 0.01. Notwithstanding, the results again demonstrate the effectiveness of dihydroxyacetone alone as a lipotropic agent.

The bar graphs of FIG. 3 demonstrate further results in which animals, namely chickens, which are non-mammals of the present invention. The experiment was carried out for a period of 30 days. Group I was comprised of 30 chickens and were designated control. The chickens comprising this group received a standard diet comprised of 10% fat, 21% protein and 69% carbohydrate. Group J received a diet of 10% fat, 21% protein and carbohydrate comprised of 66% and 3% of the diet by carbohydrate calorie mol was comprised of dihydroxyacetone. It can be seen by comparing the weight gain over a period of 30 days that control gained 640 grams per animal body weight more than the animals receiving essentially the same standard diet with 3% of the carbohydrate substituted for dihydroxyacetone. Similar dramatic inhibition against weight gain occurred when a second group of female chickens were divided into two groups, one of which was designated control and identified as Group K which received the same diet as Group I. Group L received the same diet as Group J. The results demonstrated that control gain 397 grams per animal more than the weight gain of the animals which comprised Group L and received dihydroxyacetone in the diet.

As is known, the liver, in addition to synthesizing triglycerides, also acts as a storage medium for glycogen. That is, glucose brought to the liver from the intestine via the portal vein is converted to glycogen and stored. As the need arises, glucose is re-formed from glycogen and released into the bloodstream. It has been found that by administering dihydroxyacetone over a period of time, the glycogen-storing capability of the liver is increased, accompanied by an increase in the size of the liver. This is shown in the following Table where glycogen concentration in mg/g of liver tissue and total glycogen are tabulated for four groups of rats each comprised of six animals. The experiment was carried out for a period of 30 days during which the rats comprising Group M were designated control and received a stnndard liquid laboratory diet, Lieber-DeCarli #711 Bio Serv, Inc. of French Town, N.J. The animals comprising Group N received the same standard liquid laboratory diet to which was added 124 grams of pyruvate per 1000 grams of diet and 124 grams of dihydroxyacetone 1000 grams of diet. Group O received the standard laboratory diet to which was added 124 grams of dihydroxyacetone per 1000 grams of diet and 124 grams of dextrin per 1000 grams of diet. Group P received the standard laboratory diet to which was added 124 grams of pyruvate per 1000 grams of diet and 124 grams of dextrin per 1000 grams of diet. The livers of the rats in each group were subjected to a standard acid extraction of glycogen after sacrifice.

TABLE

| | Glycogen Concentration* | | |
|---|---|---|---|
| GROUP M | GROUP N | GROUP O | GROUP P |
| 19 | 31–37 | 49 | 43 |

*mg of glycogen per gram of liver tissue

It can be seen from the foregoing Table that the rats comprising Group O experienced a significant increase in the glycogen content of liver as compared with the rats comprising control, Group M. The results also show that ingestion of pyruvate alone, Group P and ingestion of the mixture of pyruvate and dihydroxyacetone, Group N, also shows a significant increase to the glycogen concentration as compared with control, Group M. For many years, athletes have attempted by eating large amounts of carbohydrate latent meals, to increase their glycogen stores prior to an athletic event requiring long endurance or sustained high performance. The use of dihydroxyacetone or pyruvate alone or in a combination of these substances, appears to increase greatly the glycogen storage capabilities of the liver.

Although the invention has been shown in connection with certain specific embodiments, it will be readily apparent to those skilled in the art that various changes can be made to suit requirements without departing from the spirit and scope of the invention.

I claim as my invention:

1. A method for controlling the weight in an animal having normal metabolic conditions, which comprises administering orally to an animal in need thereof a therapeutically effective amount of dihydroxyacetone to induce a weight loss or to reduce an expected weight gain from a given diet.

2. The method of claim 1 in which riboflavin is administered as a mixture with dihydroxyacetone.

3. The method of claim 1 wherein dihydroxyacetone is administered for at least 15 days.

4. The method according to claim 1 wherein dihydroxyacetone is administered for 60 days.

5. The method according to claim 1 wherein body fat deposition in said mammal is effectively reduced by administering dihydroxyacetone.

6. A method for increasing the glycogen store capability in the liver of an animal under normal metabolic conditions in need thereof which comprises administering a therapeutically effective amount of dihydoxyacetone over an extended period of time to increase the glycogen storage by the liver of the animal.

7. The method according to claim 6 wherein said method includes the step of mixing with said dihydroxyacetone a therapeutically effective amount of pyruvate.

8. A method for increasing the glycogen store capability in the liver of an animal in need thereof, which comprises administering a therapeutically effective amount of pyruvate to increase the glycogen storage by the liver of the animal.

* * * * *